United States Patent
Purkait (10) Patent No.: US 7,625,405 B2
(45) Date of Patent: Dec. 1, 2009

(54) BREAST IMPLANT AND METHOD OF MANUFACTURE

(75) Inventor: Bobby Purkait, Santa Barbara, CA (US)

(73) Assignee: Neosthetic, LLC, Santa Barbara, CA (US)

( * ) Notice: Subject to any disclaimer, the term of this patent is extended or adjusted under 35 U.S.C. 154(b) by 557 days.

(21) Appl. No.: 11/349,750

(22) Filed: Feb. 8, 2006

(65) Prior Publication Data

US 2007/0185575 A1   Aug. 9, 2007

(51) Int. Cl.
*A61F 2/52* (2006.01)
*A61F 2/12* (2006.01)
*A61B 19/00* (2006.01)

(52) U.S. Cl. .................. 623/8; 623/7; 128/899
(58) Field of Classification Search ............ 623/7, 623/8; 128/899
See application file for complete search history.

(56) References Cited

U.S. PATENT DOCUMENTS

| | | | |
|---|---|---|---|
| 4,731,081 A | 3/1988 | Tiffany et al. | |
| 4,960,425 A | 10/1990 | Yan et al. | |
| 4,969,899 A * | 11/1990 | Cox, Jr. | 623/8 |
| 5,026,394 A * | 6/1991 | Baker | 623/8 |
| 5,035,249 A | 7/1991 | Sasaki et al. | |
| 5,116,371 A | 5/1992 | Christensen et al. | |
| 5,158,573 A | 10/1992 | Berg | |
| 5,219,360 A | 6/1993 | Georgiade | |
| 5,282,857 A | 2/1994 | Perry et al. | |
| 5,376,117 A * | 12/1994 | Pinchuk et al. | 623/8 |
| 5,425,762 A * | 6/1995 | Muller | 623/11.11 |
| 5,458,635 A | 10/1995 | Berman | |
| 5,480,430 A | 1/1996 | Carlisle et al. | |
| 5,534,023 A | 7/1996 | Henley | |
| 5,549,671 A | 8/1996 | Waybright et al. | |
| 5,658,329 A | 8/1997 | Purkait | |
| 5,759,204 A | 6/1998 | Seare, Jr. | |
| 5,824,081 A | 10/1998 | Knapp et al. | |
| 5,843,189 A | 12/1998 | Perouse | |
| 5,935,164 A | 8/1999 | Iversen | |
| 5,941,909 A | 8/1999 | Purkait | |
| 6,086,801 A | 7/2000 | Eaton | |
| 6,113,634 A | 9/2000 | Weber-Unger et al. | |
| 6,403,758 B1 | 6/2002 | Loomis | |
| 6,432,138 B1 | 8/2002 | Offray et al. | |
| 6,544,287 B1 * | 4/2003 | Johnson et al. | 623/7 |
| 6,749,554 B1 | 6/2004 | Snow et al. | |
| 6,802,861 B1 | 10/2004 | Hamas | |
| 6,932,840 B1 | 8/2005 | Bretz | |
| 6,955,690 B1 | 10/2005 | Cao | |
| 2005/0065616 A1 | 3/2005 | Ankorina-Stark et al. | |
| 2007/0229960 A1 * | 10/2007 | Mazurek et al. | 359/604 |

* cited by examiner

*Primary Examiner*—Thomas J Sweet
*Assistant Examiner*—Yashita Sharma
(74) *Attorney, Agent, or Firm*—Blakely Sokoloff Taylor & Zafman LLP (57) ABSTRACT

An implantable soft tissue prosthesis comprising a hollow shell formed of a flexible elastomeric envelope, the shell having an inner volume and an exterior surface, when the inner volume is filled with an elastomeric silicone tubing that is preshaped conforming to the inner volume of the shell, the prosthesis being adapted to be surgically implanted in a human breast.

1 Claim, 6 Drawing Sheets

BREAST IMPLANT AND METHOD OF MANUFACTURE

FIELD OF THE INVENTION

The present invention is generally related to soft tissue implant prostheses, such as breast, testicular, tissue expander, and facial implants, and more particularly, the invention relates to a breast implant with a filling material and its method of making such implants.

BACKGROUND OF THE INVENTION

Soft tissue medical implants such as mammary prostheses generally are made of silicone material for an elastomer shell and filling material disposed inside the shell. If the shell ruptures, either as a result of accidents or through crease-fold flaw or other modes of failure, the filling material escapes into the body. If the filling material is silicone gel, hydrogel, or gel made from natural biomaterial, the exposure of such a large volume of gel material in the body would pose a significant risk and complications for both long and short terms. The risks associated with any of the gel type material have been well documented and published in the literature.

If the filling material is saline, saline will excrete readily; however, the deflated shell must be removed and would require another surgery. In many cases, it has been reported that the small pieces and fragments of shell material might migrate to other areas causing further risks and complications.

If the filling material is hydrogel made from either synthetic or natural biopolymer, the long term risks or complications remain unknown because little data exists for tissue reactivity of these materials. Furthermore, since the chemistry and characteristics of the hydrogel are significantly different from conventional silicone gel, the acceptability of the gel made from material other than silicone still remains an issue with both physicians and patients.

Soft tissue implants, particularly breast implants, have gone through a considerable transition over several years with respect to the safety of silicone gel filling materials. As a result, a number of materials have been proposed to replace the silicone gel and saline which have been used over the past 30 years.

U.S. Pat. No. 4,731,081 to Tiffany et al., entire contents of which are incorporated herein by reference, discloses a surgically implantable mammary prosthesis that is rendered rupture-resistant by injecting a liquid with uniformly dispersed lubricating material into a flexible creasable shell during manufacture or surgical implantation. The lubricating material, such as polyvinylpyrrolidone, polyvinyl alcohol, hydroxyethyl starch, or lecithin is uniformly dispersed in a carrier inflating liquid such as normal saline.

U.S. Pat. No. 5,219,360 to Georgiade, entire contents of which are incorporated herein by reference, discloses a surgical mammary prosthesis containing a liquid-gel of cross-linked hyaluronic acid inside a medical grade elastomer, and a method of making a prosthesis containing such a liquid-gel. Because the gel used in the invention contains a nontoxic, nonantigenic, noninflammatory, biodegradable natural substance, problems attributed to or associated with previous silicone gel filled prostheses as a result of prosthesis rupture or leakage or "bleed" are avoided.

U.S. Pat. No. 5,282,857 to Perry et al., entire contents of which are incorporated herein by reference, discloses a medical implant comprising an outer envelope and a gel filler material, wherein the gel comprises water and a cellulose gelling agent. The gel in the implant may further contain a lubricating agent. The components of the gel are biocompatible and do not adversely affect human beings. Implants containing the lubricating agent have a decreased tendency of failure caused by internal friction on the envelope. The implants of the present invention have similar characteristics of the human breast.

U.S. Pat. No. 5,534,023 to Henley, entire contents of which are incorporated herein by reference, discloses an implantable prosthetic device having a biocompatible elastomeric shell and a polyphasic filler material consisting of gas-filled chambers or beads bathed in a biocompatible fluid. In a preferred embodiment the solid and gaseous phases of the filler comprise interconnecting flexible chains of small gas-filled beads. The gas-filled beads may be continuously extruded in a chain with a fiber of extrudate connecting the beads. In one embodiment, the extruded chains of beads are formed into a mass having the desired shape of the prostheses where they may be further crosslinked, then placed within an outer shell. The void space between the beads is filled with a biocompatible fluid such as saline.

U.S. Pat. No. 5,549,671 to Waybright et al., entire contents of which are incorporated herein by reference, discloses a fluid-filled mammary prosthesis for implantation beneath the skin of a patient comprising a shell and an adjunctive filler. The shell is preferably a closed silicone elastomer envelope having an interior volume and a valve for filling. The filler material is a mixture of a fluid such as saline and an adjunct consisting of a plurality of hollow silicone beads having two or more fenestrations within the wall of each bead which provide fluid communication between the outside of the bead and the hollow interior. The beads are packed into the shell prior to the introduction of fluid into the interior of the shell. The beads serve as a baffle to prevent unwanted hydraulic behavior of the fluid portion of the filler material and also serve to help maintain the anatomical profile of the implant. The hollow beads, which range in sizes from about $7/32$ inch to $1/2$ inch in inside diameter, may be conveniently made by injection molding. The adjunctive filler may be a plurality of beads of a particular size or a mixture of different sized beads.

U.S. Pat. No. 5,824,081 to Knapp et al., entire contents of which are incorporated herein by reference, discloses a tissue implant comprising a flexible shell, a fluid filler within the shell, a compound foam body disposed within the shell, the compound foam body comprising a distinct first foam region having a substantially uniform first cellular density throughout the first foam region, and a distinct second foam region having a substantially uniform second cellular density throughout the second foam region, the second cellular density being different than the first cellular density, and a cavity in the compound foam body adapted to provide a hydraulic reservoir for the fluid filler, the cavity being substantially larger than any cell.

U.S. Pat. No. 5,843,189 to Perouse, entire contents of which are incorporated herein by reference, discloses a breast prosthesis comprising a plurality of pockets filled with a liquid, wherein each of the pockets has, at rest, a predetermined configuration, and each of the pockets is delimited by a flexible membrane; and a holding device for holding the pockets against one another, wherein the pockets are formed integrally with one another so as to form at least one string.

U.S. Pat. No. 5,941,909 to Purkait, entire contents of which are incorporated herein by reference, discloses a new soft tissue implant filling material. The surgically implantable soft tissue implant filling material has good aesthetic properties, as measured by viscosity and elasticity. One embodiment of such a new filling material is a gel which comprises three components. The first component is a water soluble polymer or hydrogel that has a high molecular weight. Alternatively, the first component is both crosslinked and has a high molecular weight. The second component of the filling material is a water-soluble polymer that is eliminated rapidly through the kidneys upon subcutaneous release. The third component of this filling material is saline, which is used to dissolve the polymer and to adjust the osmolality of the polymer. In addition, a buffer may be added to the filling material to adjust the pH of the gel. One gel formulation of the present invention, in its preferred embodiment, consists of polyacrylamide and derivatives thereof.

None of the prior art patents recognize or addresses the critical and important issues which are involved in the selection of a suitable material that would provide a safe and effective implant filling material.

SUMMARY OF THE INVENTION

It is, therefore, an object of this invention to provide a mammary prosthesis with a silicone shell containing a filling material made from silicone tubing that renders the improvements and benefits as: (1) filling material being made from the same shell material family would not require any new or different biocompatible data and thus would provide a relatively faster regulatory approval; (2) issues related to gel migration, bleed and exposure of many low molecular weight chemical components to the body would be eliminated; (3) in case of rupture, the tubing bundle could be removed easily and would not migrate or excrete; (4) the manufacturing process and method of making the final product would be simple and less expensive than the current saline or gel manufacturing process; (5) in case of rupture, there will be no need to remove the implant as no functionality loss is expected thus making the implant a deflation proof prosthesis; and (6) the implant aesthetic look and feel would remain equal to or better than the current gel or saline implant.

It is a further object of this invention to provide a method of making such a compatible filling material which would provide substantially better feel and aesthetic appearance than the current prosthesis.

It is another object of the invention to provide a soft tissue prosthesis to remain functional even after shell rupture from the prosthesis, for examples, a breast, a testicular, a tissue expander, and a facial implant comprising a filling tubing material made of the same material of the shell.

Some aspects of the invention relate to an implantable soft tissue prosthesis comprising a hollow shell formed of a flexible elastomeric envelope, the shell having an inner volume and an exterior surface, when the inner volume is filled with an elastomeric silicone tubing, the prosthesis being adapted to be surgically implanted in a human breast. In one embodiment, the softness of the silicone tubing ranges from 10 D to 50 D, wherein the silicone tubing is made from medical grade silicone polymer that is platinum or peroxide cured. In one embodiment, the softness of the silicone tubing is substantially identical to that of the shell. In another embodiment, the diameter of the silicone tubing is substantially constant along its length.

One embodiment of the invention provides the envelope with means for filling the inner volume with silicone tubing, wherein the means may be a valve, a one-way check valve or a self-closing seal. In one embodiment, the silicone tubing is filled with a substance selected from the group consisting of saline, viscous saline, silicone gel, hydrogel, and thermo reversible polymeric gel. In one embodiment, the prosthesis further comprises foam with at least one closed cell having a consistent gel-like feel and durability. In another embodiment, the silicone tubing of the prosthesis is encapsulated with super absorbent hydrogel material, preferably before being filled into the envelope.

Some aspects of the invention relate to an implantable soft tissue prosthesis comprising a hollow shell formed of a flexible elastomeric envelope, the shell having an inner volume and an exterior surface, wherein when the inner volume is filled with a strip of silicone elastomer made of a material similar to the material for making the hollow shell, the prosthesis being adapted to be surgically implanted in a human body, such as a breast, a testicular, a tissue expander, and a facial.

Some aspects of the invention relate to an implantable mammary prosthesis to augment or reconstruct natural breast tissue, the prosthesis comprising a hollow shell formed of a medical grade elastomer, the hollow shell having an inner wall and an inner volume filled with silicone tubing, wherein the prosthesis is characterized with a property of non-deflation upon rupture of the shell. In one embodiment, the silicone tubing is detectable with mammography or ultrasound imaging. In another embodiment, the inner wall is coated with lubricating biocompatible polymer. In still another embodiment, the inner wall is coated with cohesive silicone elastomer selected from the group consisting of hyaluronic acid, polyvinylpyrroldine, polyvinyl alcohol, lecithin, silicone gel, polyacrylamide, polyethylene oxide, polypropylene oxide, polyethylene oxide/polypropylene oxide (PEO/PPO) combination, polycaprolactone, polylactic/polyglycolic acid, fatty acid esters, fatty acid salts, hydroxyl ethyl starch, methacrylates, and peptides.

Some aspects of the invention relate to a method of making a mammary prosthesis, comprising: providing a soft silicone tubing and a hollow shell formed of a flexible elastomeric envelope defining an inner volume; braiding and weaving the silicone tubing to form a desired shape with softness and durability; and filling the inner volume with the shaped tubing conforming to the inner volume of the shell. In one embodiment of the present invention, the soft silicone tubing is open-ended with a lumen space. In another embodiment, the soft silicone tubing is close-ended at both ends. In still another embodiment, the lumen space of the close-ended tubing is filled with a desired fluid or gel.

In one embodiment, the tubing in the method of making a mammary prosthesis has a softness between about 5 D and 100 D, preferably between about 10 D to 50 D, or has an outside diameter between about 0.1 to 0.125 inch. Preferably the tubing has an outside diameter of between about 0.15 and 0.3 inch.

Some aspects of the invention relate to a method of making a mammary prosthesis comprising providing a soft silicone tubing; braiding and weaving the silicone tubing to form a desired shape with appropriate softness and durability; dipping the shaped silicone tubing in RTV or methyl dispersion silicone to form into a self integrated implant adapted for use as the mammary prosthesis.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

The preferred embodiments of the present invention described below relate particularly to a soft tissue implant prosthesis, filling material, and its method of manufacturing. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

FIGS. 1-6 show one preferred embodiment of a mammary prosthesis according to the present invention. The present invention is a surgically implantable soft tissue implant with filling material having a number of novel characteristics, many of which have not heretofore been recognized previously or disclosed in the prior art.

Figure 1:
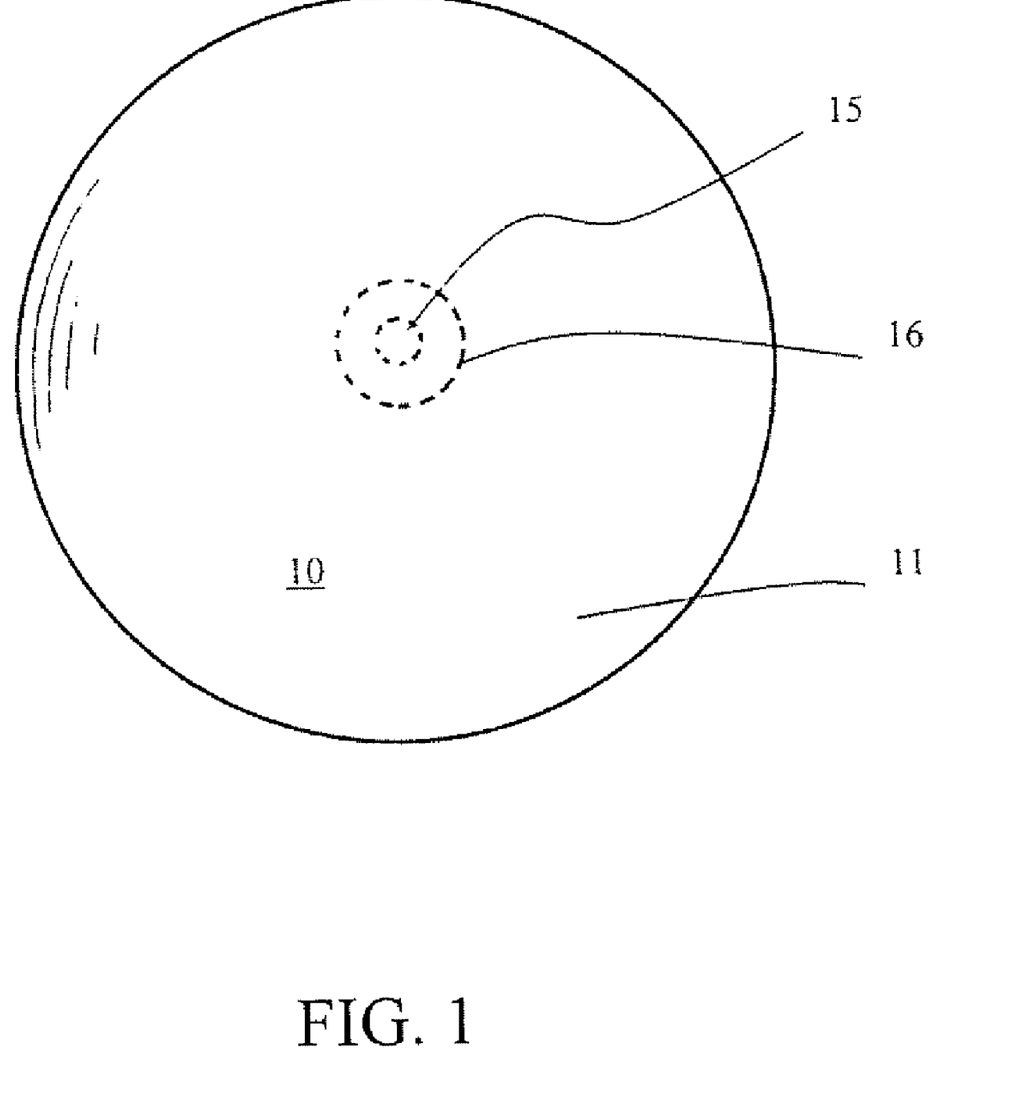
FIG. 1 shows a top view of a mammary prosthesis of the invention.
Figure 2:
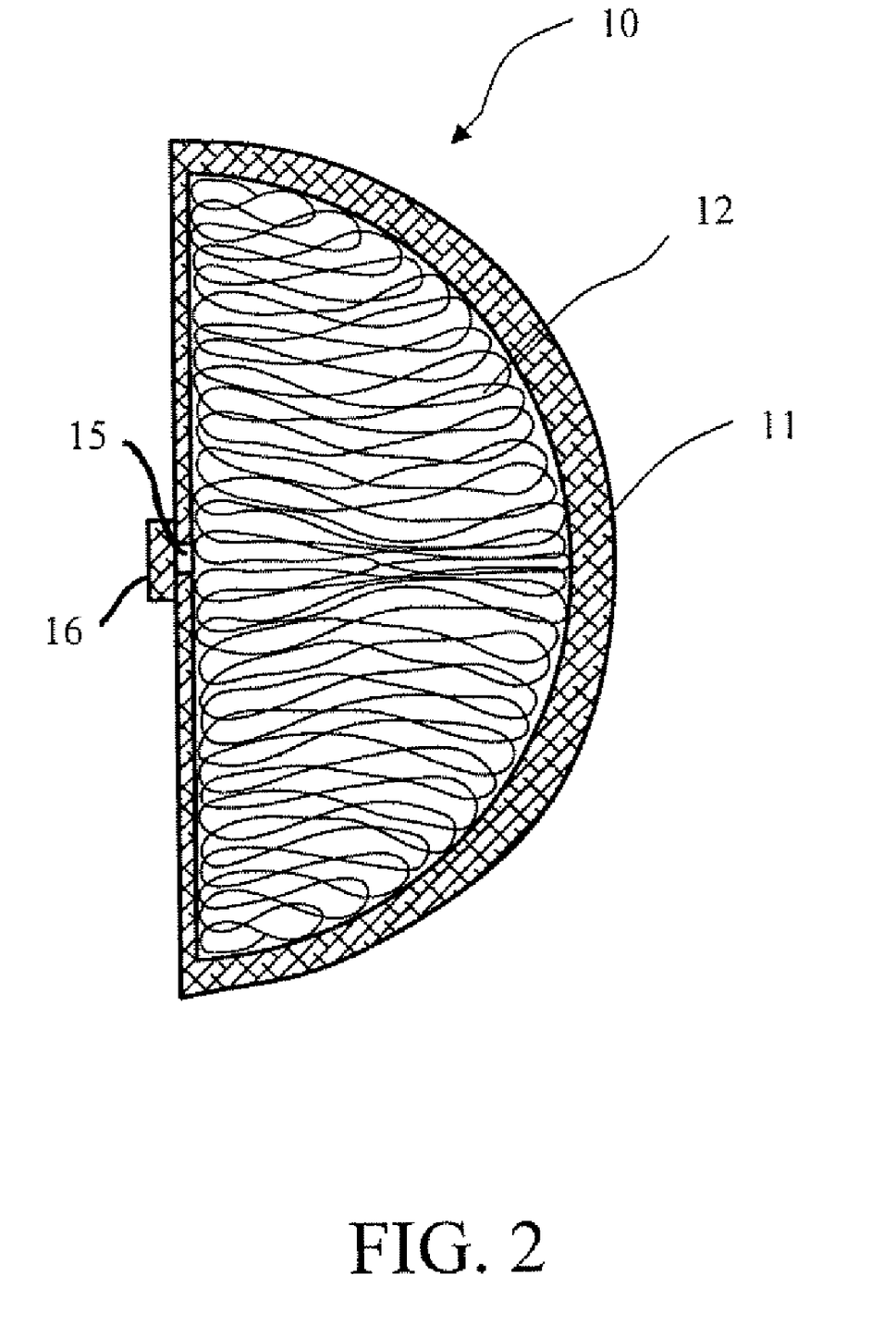
FIG. 2 shows a side cross-sectional view of the mammary prosthesis filled with a filling tubing.

FIG. 1 shows a top view of a mammary prosthesis of the invention whereas FIG. 2 shows a side cross-sectional view of the mammary prosthesis 10 filled with filling tubing 12. The invention relates to a medical implant comprising an outer envelope or shell and silicone tubing as filling material. The shell 11 may also comprise other features. In one embodiment, one silicone tubing is the sole filling material, wherein the filling tubing is sized and arranged to fill most or all of the void space within the envelope. In a further embodiment, a plurality of silicone tubings is the only filling material.

In an alternate embodiment, a small quantity of lubricants or lubricating material is added inside the envelope adapted for lubrication or friction reduction between sections of the filling tubing or between any section of the filling tubing and an interior surface of the shell. For example, lubricating material can be selected from the group consisting of silicone oil, saline, gel, hydrogel, other oil, hyaluronic acid, and the like. In a further embodiment, the lubricating material comprises a plurality of distinct, detached beads with uniform sizes or various sizes, wherein each bead consists of a shell made of the same material as that of the envelope of the mammary prosthesis. The interior of the beads is filled with gas, liquid or gel to enhance resilience or elasticity. In some embodiments of the invention, the silicone beads serve as the lubricating material in the presence of the silicone tubing or serve as the filler that replaces the silicone tubing in a mammary prosthesis. The lubricating material reduces frictional wear along opposed inner surfaces during sliding contact in a creased area in the shell wall after surgical implantation.

Figure 3:
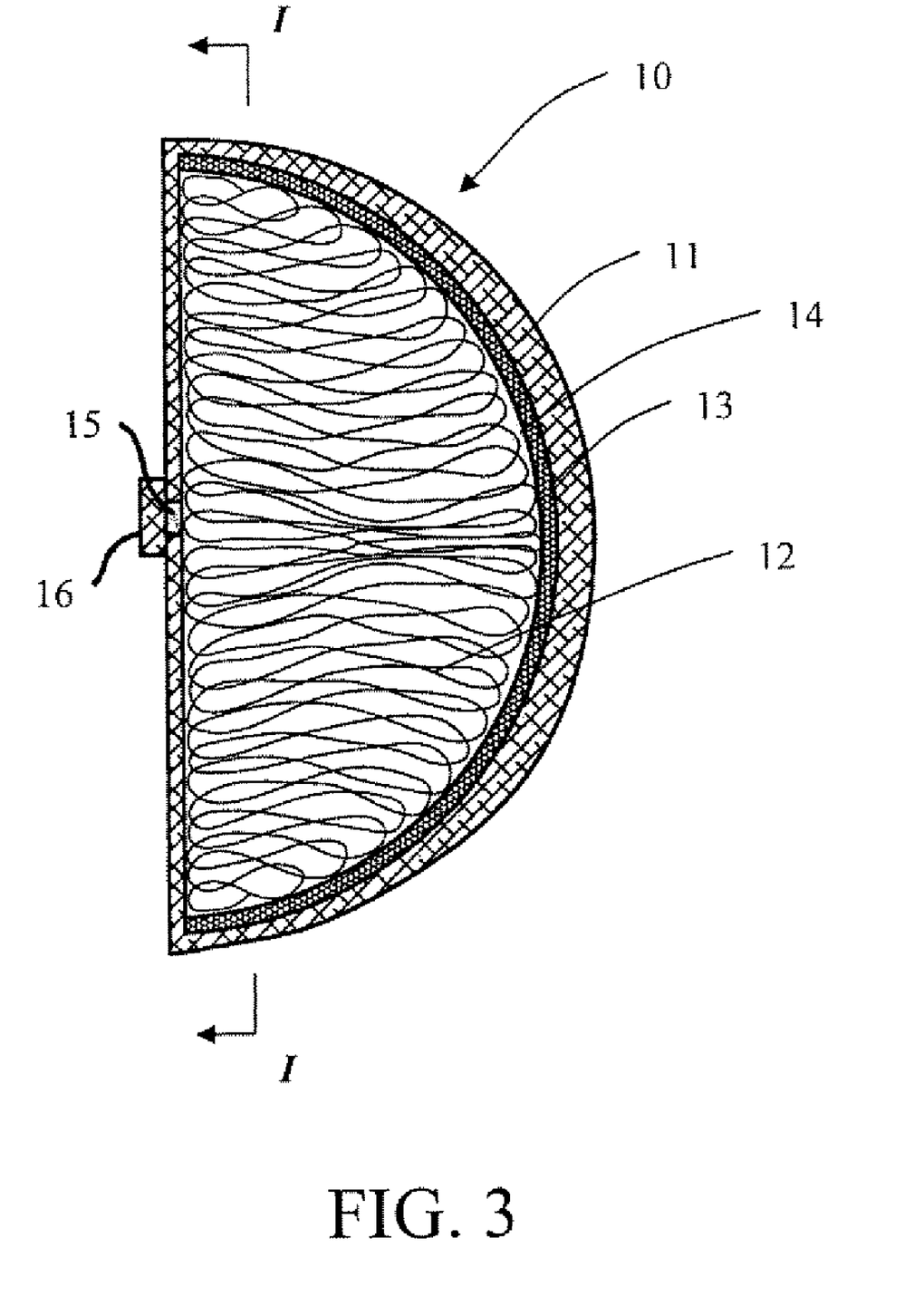
FIG. 3 shows a side cross-sectional view of the mammary prosthesis filled with a filling tubing that has a coating surface.

In one embodiment, the tubing softness is in the range from 10D to 50D (measured in durometers, D) with an outside diameter of about 0.10 inch to 0.125 inch or higher. In a further embodiment, the tubing may have a softness between about 5D and 100D. In one preferred embodiment, the tubing has an outside diameter of between about 0.15 and 0.3 inch. To maintain flexibility and integrity of the filling tubing, the tubing thickness is about 0.005 to 0.05 inch, preferably between about 0.01 to about 0.02 inch. In a preferred embodiment, the cross-section of the tubing has a pair of thicker walls opposite to each other. By ways of illustration, the average thickness of the cross-section wall of the tubing in each quadrant may be 0.01, 0.02, 0.01, 0.02 inch, respectively. Prior to filling, the tubing is wound into a desirable shape as required by the implant size with a special winding process, for example, a 3-D wound shape. The tubing is fabricated into a desired shape independently and could be inserted into the shell during final product manufacturing. The shell would be closed with a patch after filling and would be ready for sterilization. FIGS. 1, 2, and 3 show patch 16 covering opening 15. In another embodiment, the shell is formed, molded, or cast around the shaped tubing that is sized and configured to manufacture a mammary prosthesis. In an alternate embodiment, the filling tubing may be substituted by a filling strip or a flexible elongate filling belt or rod without any internal void space in the present invention.

Figure 4:
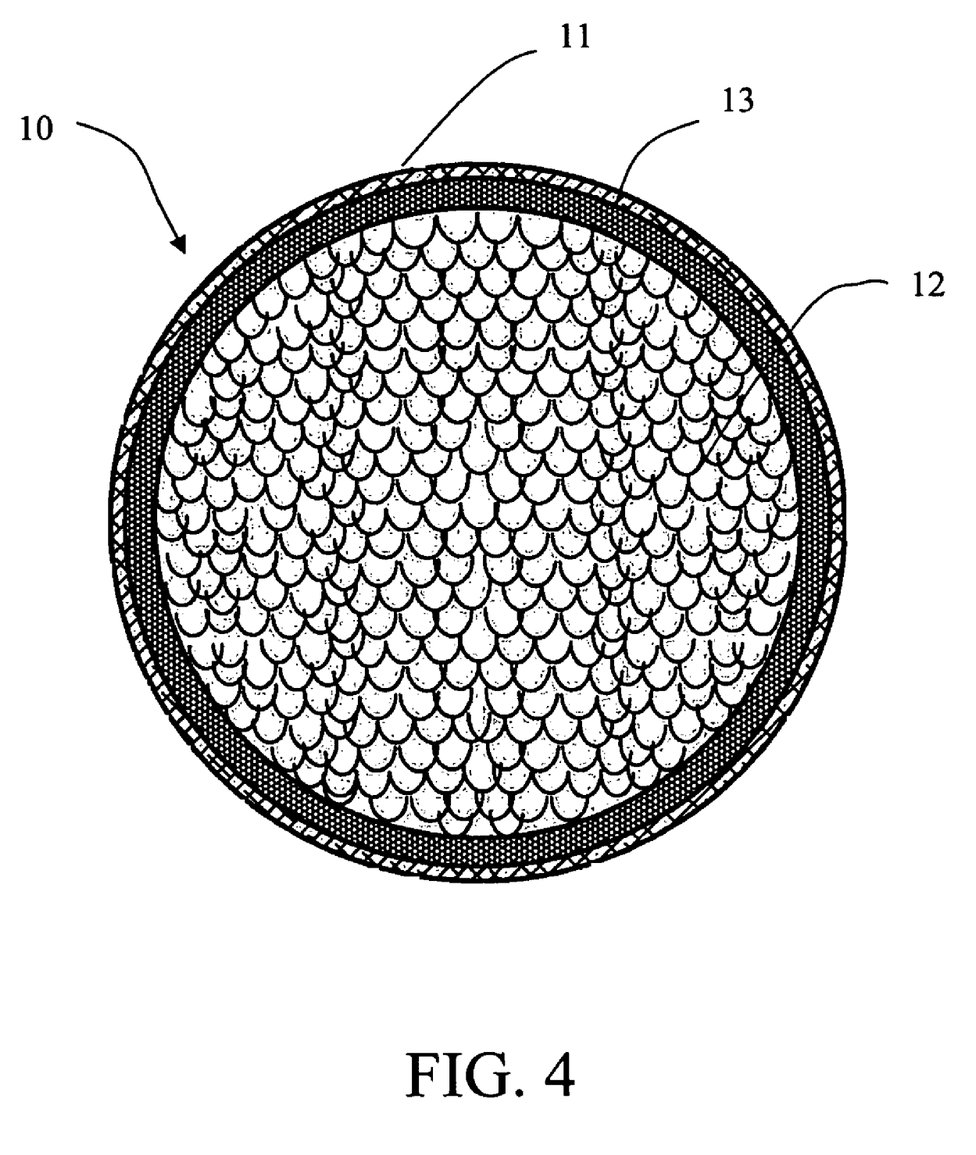
FIG. 4 shows a top cross-sectional view of the mammary prosthesis, section I-I of FIG. 3.

The implant filled with medical grade silicone filling tubing or strip with or without a textured exterior surface can be used for either augmentation or reconstruction of breast or other implantation purposes. In one embodiment, the filling tubing occupies at least 80 percent, preferably about 95%, and most preferably about 99% or more, of the interior volume 14 of the elastic envelope 11 or prosthetic shell. By ways of illustration, high density packing may be achieved by laying the tubing snugly along the recessed interface of the wound pattern in a 3-dimensional manner. FIG. 3 shows a side cross-sectional view of the mammary prosthesis filled with a filling tubing that has a coating surface whereas FIG. 4 shows a top cross-sectional view of the mammary prosthesis, section I-I of FIG. 3.

In one embodiment, the silicone tubing is substantially uniform in diameter or cross-sectional area/shape along the length of the tubing. In another embodiment, the cross-sectional area may be a circular shape, an oval shape, a semi-circular shape, a rectangular shape, or other shape. When the interior void of the filling tubing is filled with a fluid or gel, the fluid/gel is not in communication with the exterior portion of the filling tubing. In one embodiment of the present invention, the soft silicone tubing is open-ended with a lumen space. In another embodiment, the soft silicone tubing is close-ended at both ends. In still another embodiment, the lumen space of the close-ended tubing is filled with a desired fluid or gel.

In another aspect, the invention relates to a method of preparing tubing wound in a suitable shape resulting in the desired softness and volume for the implant to achieve intended purposes. In one embodiment, the tubing is formed into a flexible woven ball conforming to the inner volume or inner space of the shell. In another embodiment, the silicone tubing is braided and/or woven to form a desired shape with appropriate softness and durability.

Figure 5:
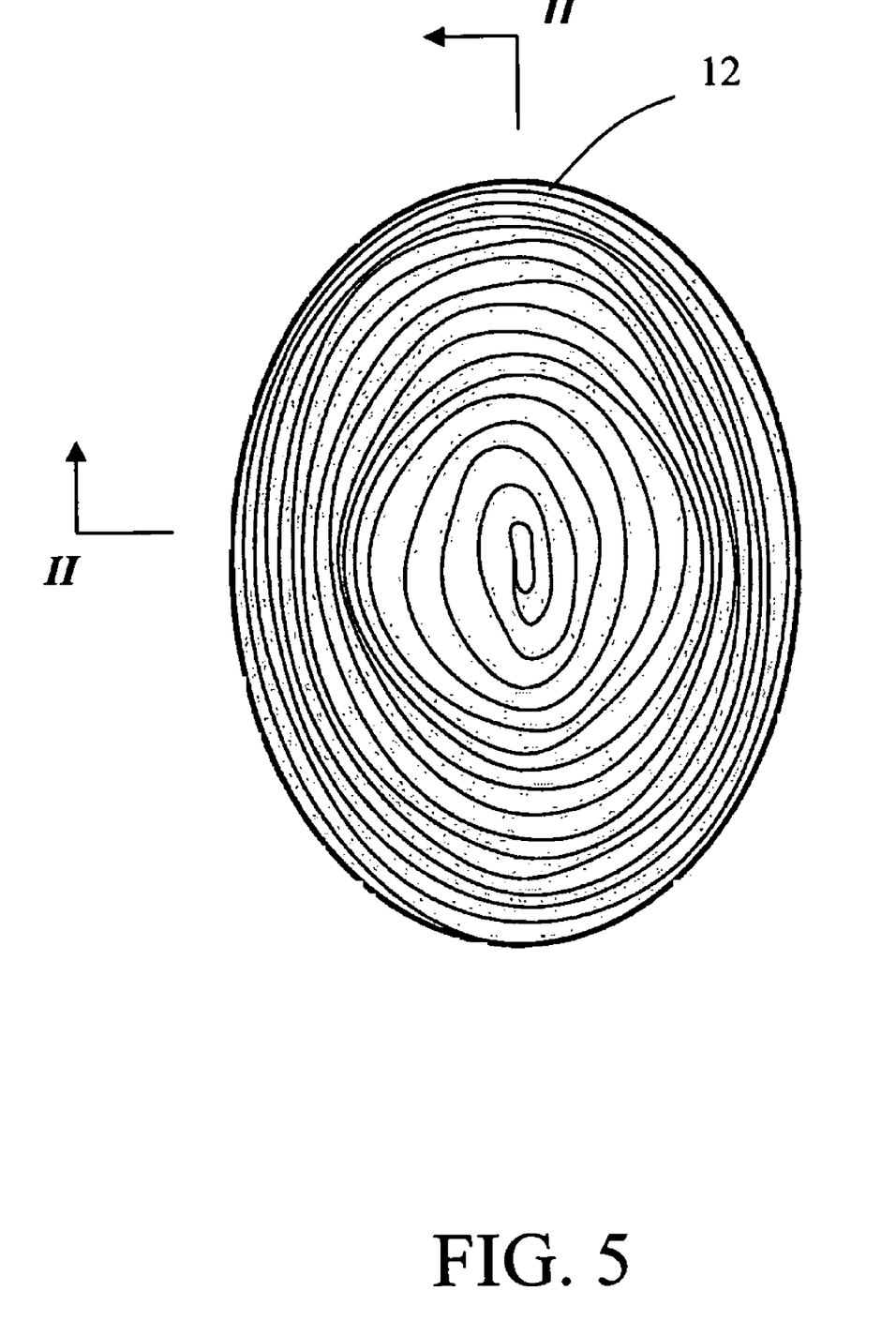
FIG. 5 shows one embodiment of the wound tubing prior to being inserted into a shell of the empty mammary prosthesis.
Figure 6:
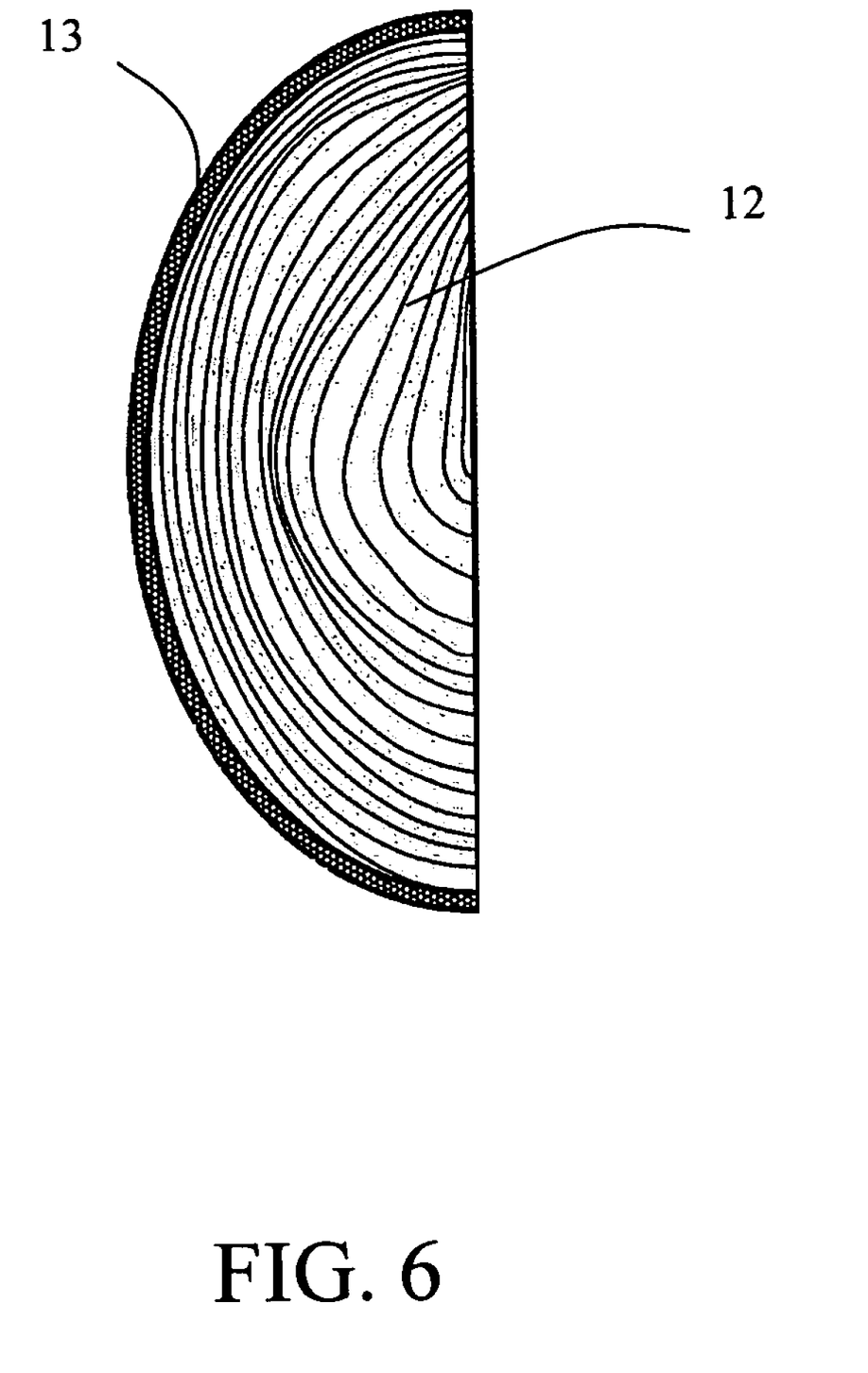
FIG. 6 shows half of the cross-sectional view of the wound tubing with surface coating, section II-II of FIG. 5.

FIG. 5 shows one embodiment of the wound tubing prior to being inserted into a shell of the empty mammary prosthesis whereas FIG. 6 shows half of the cross-sectional view of the wound tubing with surface coating, section II-II of FIG. 5. In one embodiment, the tubing is wound in a continuous 3-dimensional circular manner similar to a circular-shaped pyramid.

In other aspects, the invention relates to a special RTV (room temperature vulcanized silicone) coating as a skin 13 over at least a portion of the wound tubing to ensure the wound tubing holds its shape properly and uniformly. Furthermore, the coating would prevent abrasion of the tubing with the shell and thus would provide a longer life of the implant. The thickness and softness of the coating would further enhance the feel and aesthetic appearance of the implant. In a further embodiment, the coating would fill up the void in between exterior surfaces of the wound tubing; increase the occupied volume of the shell space, thus making a low void mammary prosthesis feasible.

The invention also relates to silicone filling tubing that contains a thermo reversible hydrogel, viscous saline made with viscosity enhancer polymer, or viscous gel inside the sealed or close-ended tubing. In one embodiment, the silicone tubing contains self-expanding foam or sponge inside the sealed tubing, wherein the self-expanding foam or sponge is triggered to expand by a remote ultrasound, radiofrequency or electromagnetic energy. The expanded filling tubing would occupy the interior void space of the envelope to a desired percentage. The foam or sponge matrix, after expanding, is configured sufficiently resilient to support the envelope without collapsing.

Some aspects of the invention relate to a medical implant such as a mammary prosthesis that is rendered deflation resistant due to filling with silicone tubing as a novel solid filling material. In one embodiment, the tubing is filled with saline or thermo reversible polymeric hydrogel. In another embodiment, the mammary prosthesis is filled with at least one elastomer strip made of silicone. Because the filling tubing or the filling strip used in the invention is made from the identical material used in the envelope or shell of the prosthesis, the biocompatibility, overall safety and efficacy data that currently exist would apply for the filling tubing material.

Additionally, problems attributed to or associated with silicone gel filled prosthesis as a result of prosthesis rupture or leakage or bleed could be avoided. Rupture or deflation of a saline mammary prosthesis would require the shell to be removed as the deflated shell would loose its functionality. The mammary prosthesis of the present invention would remain functional and might not need to be removed upon rupture of the shell because the shaped silicone tubing would retain its shape and strength and would likely maintain its functionality.

In case of a catastrophic failure of the envelope, the filler tubing or strip material (elongate filling material) could be removed easily by pulling one end of the silicone filling tubing/strip and the whole elongate filling material is removed thereafter. However, the gel filling material of a conventional mammary prosthesis would disperse to other parts of the tissue and would potentially pose a long term risks.

The novel and unique characteristics of the invention are outlined as follows:
1) the filling tubing or strip made from identical material as shell is compatible with the shell and other components of the implant;
2) the filling tubing or strip would not migrate, does not have bleed, will not collapse because of rupture, can be easily retrieved, will not interfere with mammography and will remain stable and last longer even upon the rupture of the shell;
3) the softness, feel and consistency of prosthesis (shape and volume) will be controlled by the winding technique and method of winding for the filling tubing;
4) due to the identical chemical, physical and biological properties of the filling tubing with the shell material, the regulatory requirements will be similar. As a result the submission for regulatory approval would be faster and less burden; and
5) the manufacturing of the breast prosthesis would be less expensive as winding of the filling tubing could be done separately and the final product could be assembled by inserting the wound tubing and patching the shell.

From the foregoing, it should now be appreciated that a mammary prosthesis filled with filling tubing or strip of the same shell material has been disclosed. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. An implantable soft tissue prosthesis adapted to be surgically implanted in a human breast consisting essentially of a hollow outer shell defining an inner void volume filled with an elastomeric silicone unfilled tubing,
   said outer shell is formed of a flexible elastomeric envelope and wherein said unfilled tubing is of medical grade platinum or peroxide cured silicone polymer;
   said elastomeric silicone tubing having a length and an outside diameter substantially uniform along said length of between about 0.1 and 0.125 inch, a thickness between about 0.005 and 0.05 inch, and a softness ranging from about 5D to 50 D;
   and wherein the void between said silicone tubing being unfilled.

* * * * *

UNITED STATES PATENT AND TRADEMARK OFFICE
CERTIFICATE OF CORRECTION

PATENT NO.       : 7,625,405 B2
APPLICATION NO. : 11/349750
DATED            : December 1, 2009
INVENTOR(S)      : Bobby Purkait It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 853 days.

Signed and Sealed this

Twenty-sixth Day of October, 2010

David J. Kappos
*Director of the United States Patent and Trademark Office*